(12) United States Patent
Uribe

(10) Patent No.: US 6,715,603 B1
(45) Date of Patent: Apr. 6, 2004

(54) DENTAL CARE KIT

(76) Inventor: Juan Carlos Uribe, 1440 SW. 78th Ave., Miami, FL (US) 33144

( * ) Notice: Subject to any disclaimer, the term of this patent is extended or adjusted under 35 U.S.C. 154(b) by 0 days.

(21) Appl. No.: 10/022,602

(22) Filed: Dec. 17, 2001

(51) Int. Cl.[7] .............................................. A61B 17/06
(52) U.S. Cl. ...................................... 206/63.5; 206/232
(58) Field of Search ................................ 206/232, 581, 206/63.5, 359, 493, 368, 369; 132/306, 309, 312, 315

(56) References Cited

U.S. PATENT DOCUMENTS

| | | | | |
|---|---|---|---|---|
| 3,746,017 A | * | 7/1973 | Casselman .................. 132/325 |
| 3,890,986 A | * | 6/1975 | Gerlich ....................... 132/309 |
| 4,576,190 A | | 3/1986 | Youssef |
| 4,828,113 A | | 5/1989 | Friedland et al. |
| 4,972,946 A | * | 11/1990 | Whittaker ................... 206/210 |
| 5,065,861 A | * | 11/1991 | Greene et al. .............. 206/63.5 |
| 5,076,423 A | * | 12/1991 | Russack ..................... 206/63.5 |
| 5,181,531 A | | 1/1993 | Escoto et al. |
| 5,215,193 A | * | 6/1993 | Dennis ........................ 206/223 |
| 5,365,874 A | * | 11/1994 | Dorfman .................... 116/200 |
| 5,445,825 A | | 8/1995 | Copelan et al. |
| 5,487,201 A | | 1/1996 | Hansen et al. |
| 5,678,580 A | * | 10/1997 | Sherman ..................... 132/324 |
| 5,819,765 A | * | 10/1998 | Mittiga ....................... 132/309 |
| 5,913,418 A | * | 6/1999 | Singh ......................... 206/63.5 |
| 5,950,641 A | * | 9/1999 | Taveras ...................... 132/309 |
| 6,206,192 B1 | * | 3/2001 | Winstead et al. ........... 206/572 |

* cited by examiner

Primary Examiner—Shian Luong
(74) Attorney, Agent, or Firm—Malloy & Malloy, P.A.

(57) ABSTRACT

A dental care kit assembly having a plurality of operative components such as one or more dental floss assemblies and a cleaning implement located within separated areas or compartments of a container. The container has a substantially flat, predetermined, reduced size configuration, closely corresponding to the size of a conventional credit card thereby enabling it to be conveniently carried on the person of a user. The reduced size container and the various components contained therein may be structured to be disposable after a single or a limited number of uses or alternatively may be of a more permanent structure capable of being used over a more extended period of time.

40 Claims, 3 Drawing Sheets

DENTAL CARE KIT

BACKGROUND OF THE INVENTION

1. Field of the Invention

A dental care kit assembly including a container having predetermined, reduced size configuration and a plurality of operative components including dental floss, a cleaning implement, etc. for the practice of dental hygiene at almost any location or environment where a conventional toothbrush or other dental hygiene facilities are typically not available.

2. Description of the Related Art

The problems associated with maintaining proper dental hygiene in a variety of locations where conventional cleaning implements, such as a toothbrush, etc. are not commonly available, are widespread. In addition to the general population, those individuals being fitted with some type orthodontic appliance, such as braces, may encounter unusual difficulty in maintaining the desired quality of dental hygiene. Known attempts to overcome such problems generally include the combined packaging of items such as dental floss, one or more additional cleaning instruments, a supply of dentifrice, etc. In many cases such dental care products are collectively assembled in a consolidated package in order to make such hygiene assemblies more convenient for use. However, the vast majority of known assemblies of this type are still relatively bulky and are commonly associated with a package or container which stores or contains the various components in the same compartment or areas.

One problem associated with packaging of the type described above is a likelihood of contamination of all of the dental care products if and when at least one of such products, such as a cleaning instrument, has been utilized and replaced in the package. Also, while the provision of dental floss is common practice in such dental hygiene assemblies, it is normally provided in a relatively small quantity such as a single strand. Moreover, when provided, the strand of dental floss is frequently stored in an area where removal of a segment of such strand, having a preferred length, is difficult if not impossible. Accordingly a user is forced to use substantially the entire strand and then discard the strand after use. Moreover, if more than one dental floss strand is provided, the strands may be packaged in a common area and not sufficiently separated or independently mounted to prevent tangling thereof.

It is also well known, to use some type of cleaning instrument which frequently resembles at least a portion of a conventional toothbrush at least in terms of function if not specific structure. Such a cleaning implement has been known to take a variety of different structural embodiments including various devices which fit on or about one or more fingers of the user. A cleaning segment of such implement may be in the form of outwardly directed bristles, cleaning materials or the like which are intended to come into direct contact with the teeth and gums of the user. While intended for only temporary use, such cleaning instruments have been recognized as being generally inefficient, especially when it is intended to combine or add to such implements a dentifrice in the form of a gel, paste, power, etc.

When assemblies and the various products of the type set forth above are utilized, the user frequently enjoys minimal benefits in terms of adequate dental hygiene and often must endure a messy and ineffective procedure in attempting to reach the various areas of the teeth and gums required to be cleaned. Also, use of such known and conventional dental hygiene assemblies typically requires the various components to be discarded immediately after use in order to avoid contamination of all of the commonly packaged components even when only one of such components has been used.

Accordingly, based on the above recognized problems associated with such known dental hygiene assemblies, there is a need in this area for an improved dental care assembly, which is preferably provided or made available in a kit format. Such an improved or preferred dental care kit assembly should include operative components which are structured for efficient use and preferably contained or packaged in separate or segregated areas of a container. Also, the various structural and operative components of a preferred dental care kit assembly should be particularly adapted to facilitate the cleaning of the mouth of individuals having various types of orthodontic appliances. At the same time, the operative and structural components of a preferred and improved dental care kit assembly should be capable of providing the desired degree of dental hygiene to those users without any type of orthodontic appliances.

The container should be of a reduced size and configuration and more preferably correspond to the size of a credit card. Such an improved dental care kit assembly could therefore be located within any convenient place on a person's clothing, wallet, purse, etc. As such an improved dental care kit assembly could be used in almost any location where a toothbrush or other conventional hygiene products are not conveniently available. Further, the various operative components contained within the improved dental care kit assembly would be sufficient in quantity and uniquely structured so as to serve one or more users without fear of contamination of the remaining unused components or remaining quantities thereof.

In addition, a preferred and improved dental care kit assembly, of the type described in greater detail hereinafter, could be structured to be disposable after a single or limited use of the various components associated therewith. Alternatively, the improved assembly could be structured to have a more extended operable life, wherein its various components could be repeatedly used and subsequently stored in segregated locations, thereby eliminating the fear of contamination between users. Also such an improved dental care kit assembly could include at least some operative components which are structured for a single use and disposal thereafter. Such "replaceable" components would then be replaced by new components and stored in the aforementioned container, especially when the container and the remainder of the dental care kit assembly is intended for repeated or extended use.

Also, the structural features and/or the materials from which the container and the operative components are formed should be inexpensive, whether the dental care kit assembly is intended for disposal after limited use or for a more extended operable life. Finally, the container should have sufficient structural integrity to resist folding, collapse or other manipulation which would derogatorily effect or damage the operative components or the container itself.

SUMMARY OF THE INVENTION

The present invention is directed to a dental care assembly preferably provided in a kit format which is structured to be either disposable after limited use or capable of being used repeatedly for a period of time. The versatility of the dental care kit assembly is significantly enhanced by the structuring thereof to include a predetermined, reduced size configuration. Accordingly, a preferred embodiment, to be described in greater detail hereinafter, closely resembles the overall dimension and configuration of a conventional credit card, debit card or like structure.

More specifically, the dental care kit assembly of the present invention comprises a container preferably having a flat configuration characterized by a significantly reduced thickness. The thickness of the container is primarily dictated by the dimension and configuration of the operative components contained therein. Therefore, the predetermined, reduced size configuration enables the entire kit assembly to be carried in a variety of convenient locations on the person of the user or within a purse, wallet, etc. typically carried by a user.

In order to provide a user with proper dental care and/or hygiene, the aforementioned operative components of which the kit assembly is comprised should be such as to provide adequate cleaning of the user's teeth, mouth, etc. whether or not the user is fitted with one or more orthodontic appliances. As such, the various operative components contained in or supplied with the kit assembly of the present invention include at least one supply of dental floss. The dental floss supply may include one or more dental floss strands removably mounted on a spool or like structure. In turn, the spool is rotatably disposed within a specific area or compartment of the container. Segments of the dental floss strand are easily removed from the container and the rotatable spool through the provision of an appropriately located access assembly associated with the reduced size container.

In addition, the dental care kit assembly of the present invention comprises a cleaning implement which is structured to facilitate the brushing, polishing or other cleaning procedure on the teeth and gums. At the same time, the cleaning implement should be adapted to clean the mouth, teeth, etc, of a user wearing braces or other orthodontic appliances As such, the cleaning implement includes a handle portion and at least one, but in certain embodiments of the present invention, a plurality of cleaning heads. The one or more cleaning heads comprise a plurality of bristles or other cleaning material and are each removably secured to the handle portion in an operative position. When assembled, the handle portion and the cleaning head secured thereto allow at least a temporary cleaning action to be performed on the teeth and/or gums, such as after a meal or snack, particularly when the use of a conventional toothbrush is not convenient or possible. To facilitate frequent and convenient use of the cleaning implement, it is maintained within the preferred reduced size and configuration parameters which enable the container to have the aforementioned predetermined, reduced size configuration.

In certain preferred embodiments of the present invention, each of a plurality of cleaning heads are maintained in a substantially segregated relation to one another as well as the exterior of the container, thereby assuring that each of the cleaning heads are clean and/or have not been previously used. After use each of the cleaning heads may be discarded to avoid reuse and the possible contamination associated therewith. Also a single dental care kit assembly incorporating a plurality of cleaning heads may be utilized by different users, each choosing a different cleaning head which is maintained in segregated and possibly sterile environment prior to use.

Another feature of the kit assembly of the present invention comprises an access assembly cooperatively structured with the container so as to allow independent access to and removal of various components or contents of the container which define the care kit assembly. More specifically, the access assembly may include a plurality of different access structures each providing access to at least one area or compartment of the container. Further, the plurality of access structures are disposed and dimensioned to facilitate independent access to the different types of components.

By way of example, at least one of the plurality of access structures is disposed substantially adjacent the at least one dental floss supply and is structured to allow removal of dental floss strand segments of various lengths from the rotatable spool. In addition, a stop member may comprise a part of the first access structure or be directly associated therewith. As such, a strand segment exiting the container, once separated from the rotatable spool, may be severed by minimal forced engagement with the stop member which may include a severing portion thereon. Similarly, as will be described in greater detail hereinafter, others of the plurality of access structures defining the access assembly are disposed to allow independent access to the handle portion and/or one or more cleaning heads defining the cleaning implement.

Accordingly, the dental care kit assembly of the present invention is specifically structured to provide sufficient dental hygiene to one more users in a convenient manner and in almost any environment or location due at least in part to its preferred, predetermined, reduced size configuration. Also, as set forth above, the various components of the dental care kit assembly, as well as the container thereof may be produced from an inexpensive, disposable material thereby allowing the entire kit assembly and/or the various components thereof to be individually or collectively discarded after use. Alternatively, the container and the various operative components contained therein may be intended for a more prolonged and/or repeated use until the various operative components, such as the dental floss supply has been depleted.

These and other objects, features and advantages of the present invention will become more clear when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 5:
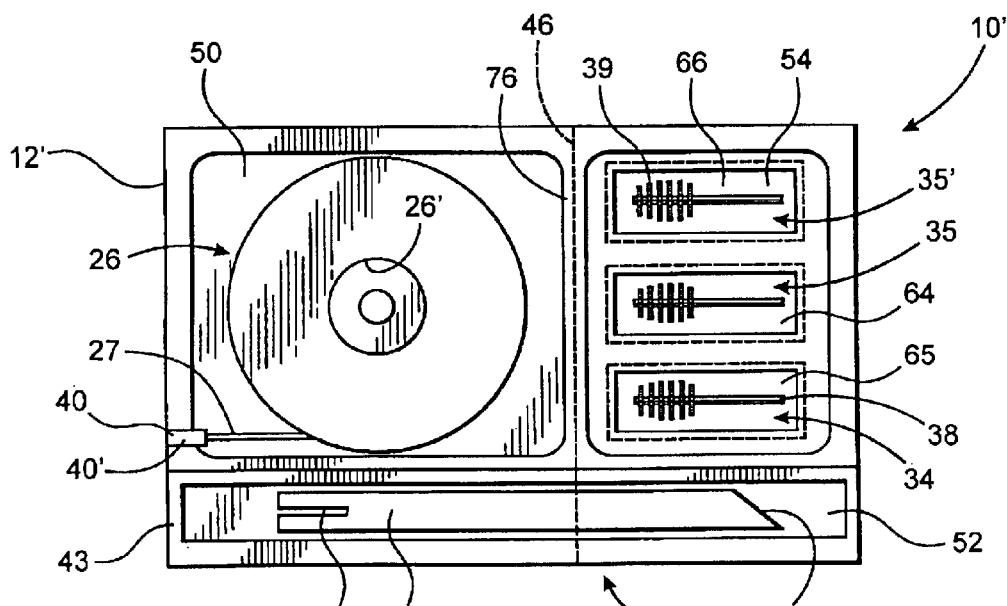
FIG. 5 is a top plan view of yet another embodiment of the present invention.
Figure 6:
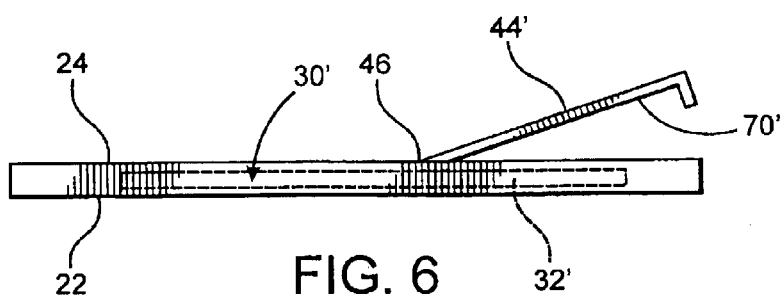
FIG. 6 is a longitudinal side view of the embodiment of FIG. 5.
Figure 7:
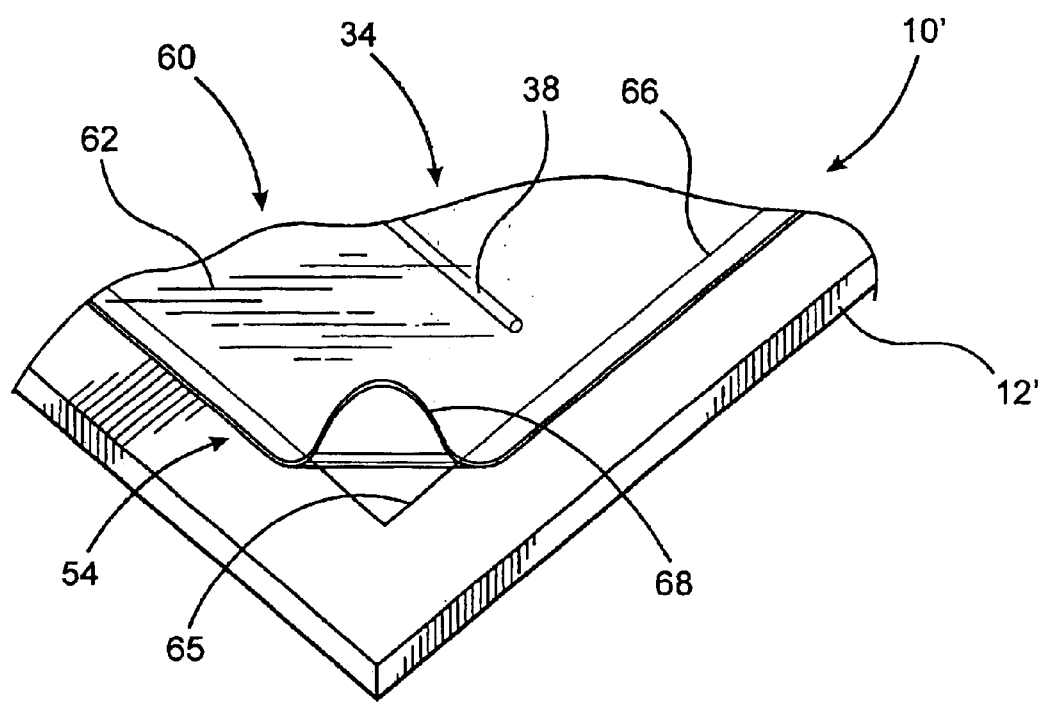
FIG. 7 is a perspective view in partial cutaway showing a portion of the embodiment of FIGS. 5 and 6.

As shown in the accompanying Figures, the present invention is directed to a dental care kit assembly generally indicated as 10 in FIGS. 1 through 4 and as 101 in FIGS. 5 through 7. The two preferred embodiments of the kit assemblies 10 and 10' differ from one another in various ways, to be described in greater detail hereinafter. It is emphasized that the structural details, dimensions, configurations, etc. of both embodiments are encompassed within the intended spirit and scope of the present invention.

First with regard to the embodiment of FIGS. 1 through 4, the kit assembly 10 includes a container generally indicated as 12 structurally characterized by having a predetermined, reduced size configuration. The reduced size configuration enhances the versatility and convenience of use of the kit assembly 10 by allowing it to be carried in almost any conventional location on a persons body, clothing, wallet, purse, etc. More specifically, the container 12 comprises a substantially flat configuration as clearly demonstrated in FIGS. 2 and 3 and has a width and length generally similar to that of a credit card.

Figure 2:
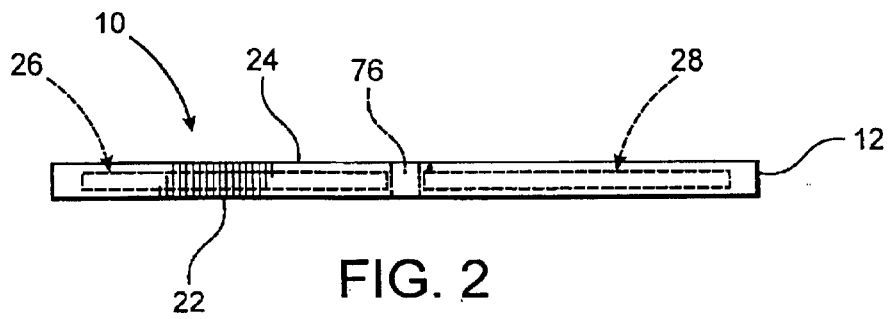
FIG. 2 is a longitudinal side view of the embodiment of FIG. 1.

With specific reference to FIGS. 2 and 3 the thickness or transverse dimension of the container 12 is substantially reduced and is effectively limited only by the content of the container 12 including the various operative components of the dental care kit assembly 10, as will be described in detail.

The container 12, in at least one preferred embodiment, includes a plurality of compartments such as 14, 16, 18, 20, etc. The number of the plurality of compartments may vary in accord with the number, dimension and configuration of the operative components contained therein. Further, at least some of the compartments as at 14, 16, 18 may be at least partially segregated from one another in order to separate the various operative components of the kit assembly 10 for reasons which will be clarified hereinafter. It is of course understood, that the container 12 may include a more simplistic structure which does not include specifically segregated compartments 14, 16, etc. but which most practically does include interior areas which serve to at least minimally separate the various operative components.

Accordingly, in the various structural modifications, as generally outlined above, the container 12 includes a base or bottom portion 22 and an overlying front panel 24. The base 22 and front panel 24 may be integrally secured to one another or may be fixedly connected as by adhesive, heat sealing, etc. Also the material from which the container 12 is formed is preferably an inexpensive yet durable, relatively high strength plastic material which is resistant to folding and/or collapse in order to at least minimally protect the operative components of the kit assembly 10 as well as the structural integrity of the container 12 itself. Further, the material from which the container is formed may be specifically intended to be discarded after a single or reasonable amount of use or may be intended for a longer operable life. In the latter situation, the various operative components of the kit assembly 10 may be replaced and stored within the container 12 after single or multiple uses.

Further with regard to the preferred embodiment of FIGS. 1 through 4, the kit assembly 10 of the present invention includes, as its various operative components, at least one but preferably two separate dental floss supplies 26 and 28. At least one but preferably both of the dental floss supplies 26 and 28 include a supply of dental floss in strand form removably mounted on a rotatable spool as at 26' and 28' respectively. As shown, each of the supplies 26 and 28 are mounted in segregated relation to one another in separate compartments 14 and 16. As set forth above, the separate compartments may be more simplistically defined by segregated areas rather than specifically formed compartment structures. Each of the dental floss supplies 26 and 28 may include the substantially same type, shape, etc. of dental floss. However, more practically the types or structures of the dental floss defining the separate supplies 26 and 28 may differ.

By way of example, one of the dental floss supplies 26 may be a thin thread like configuration wherein the other of the dental floss supplies 28 may have a ribbon type of configuration. Moreover, additional distinguishing features which may be a benefit to one or more users of the kit assembly 10 may include one or both of the dental floss supplies 26 and 28 structured to include different medications, flavorings, colorings, etc. as will be discussed further. Also each of the dental floss supplies 26 and 28 may include one or more elongated strands 27 and 29 removably supported on the spools 26' and 28' respectively and thereby easily removable therefrom, independently of one another through an access assembly, which will be described in greater detail hereinafter.

The operative components of the dental care kit assembly further includes a cleaning implement generally indicated as 30. The cleaning implement 30 preferably includes a handle portion 32 and at least one cleaning head 34. As shown, at least one of the preferred embodiments of the dental care kit assembly 10 may include a plurality of cleaning heads as at 34 and 35. The provision of a plurality of cleaning heads allows discarding of each cleaning head after a single use or allows for separate users to use the individual cleaning heads 34 and 35. Afer use, the separate cleaning heads may be discarded and/or returned to individual segregated compartments 18, 20.

In order to enhance the versatility of the dental care kit assembly 10, at least to the extent of facilitating use of a plurality of different cleaning heads 34 and 35, each of the cleaning heads may be removably secured to the handle portion 32 so as to extend outwardly therefrom in an operative position. More specifically, the handle portion 32 includes at least one receiving socket 36 which is dimensioned and configured to firmly, but removably receive and secure a stem portion 38 of the one or more cleaning heads 34 and 35. The outward orientation of the one or more cleaning heads from the handle portion 32 is such as to facilitate the cleaning of the teeth and/or gums in an intended and preferred manner. In addition to the elongated steam 38, each of the cleaning heads 34, 35, etc. includes an array or grouping of bristles structured and secured to the stem 38 so as to extend outwardly therefrom. The bristles may assume a variety of different, configurations, materials, etc. but should be structured to facilitate the brushing or otherwise cleaning of the teeth, gums and interior of the mouth of a user who may or may not be fitted with braces or a variety of other orthodontic appliances.

Yet another feature of the various preferred embodiments of the present invention is the provision of an access assembly which facilitates independent access to and removal of the various operative components of the kit assembly 10 from the container 12. To accomplish such independent access, the access assembly comprises a plurality of access structures each of which are disposed in cooperative relation to a specific compartment or interior area of the container 12 to thereby enhance the aforementioned independent access.

As such, the plurality of access structures include at least one access structure in the form of an access aperture or opening 40 and 42 respectively disposed to provide access to the interior of the area or compartments 14 and 16. Further the access openings 40 and 42 are structured to allow removal of the dental floss strands 27 and 29 from the respective supplies 26 and 28. Further, the access structures 40 and 42 include or are directly associated with a stop member 40' and 42' which are structured to engage and retain the individual strands 27 and 29 as they exit from the interior compartments 14 and 16. The stop members 40' and 42' also include a severing portion comprising any of a variety of different types of blades or cutting edges. Minimal forced engagement of the strands 27 and 29 with the severing portion of the stop members 40' and 42' will cause the removal and separation of a strand segment extending outwardly from the exterior of the container 12.

Figure 1:
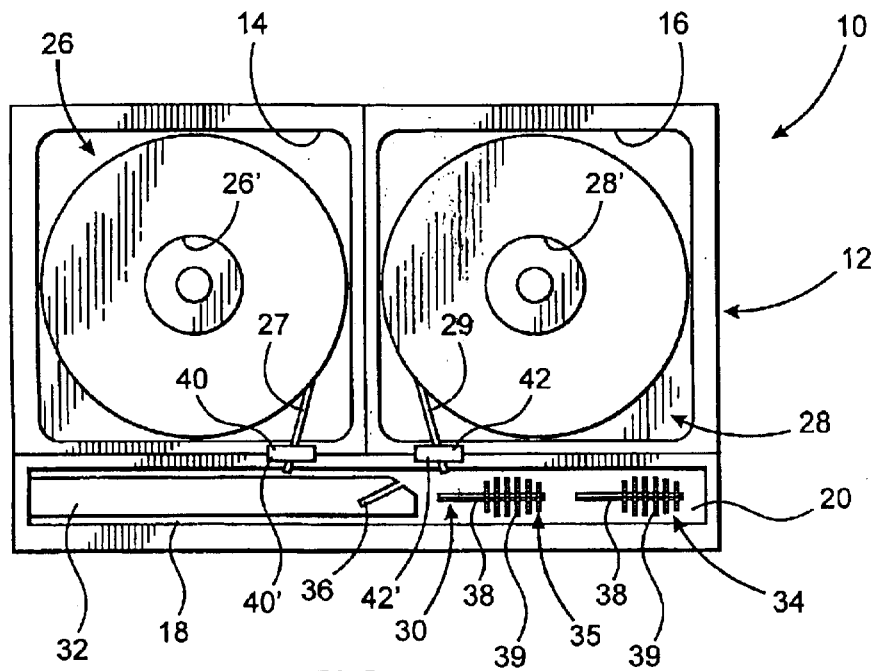
FIG. 1 is a top plan view of one preferred embodiment of a dental care kit assembly of the present invention.
Figure 3:
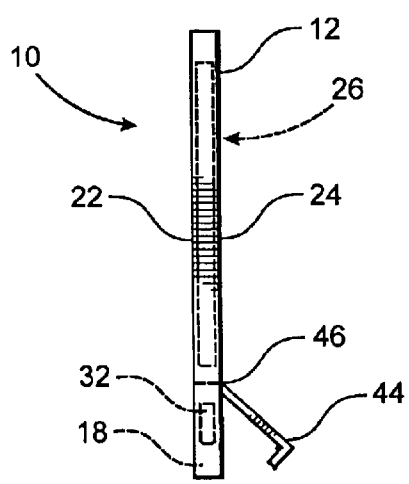
FIG. 3 is an end view of the embodiment of FIGS. 1 and 2.
Figure 4:
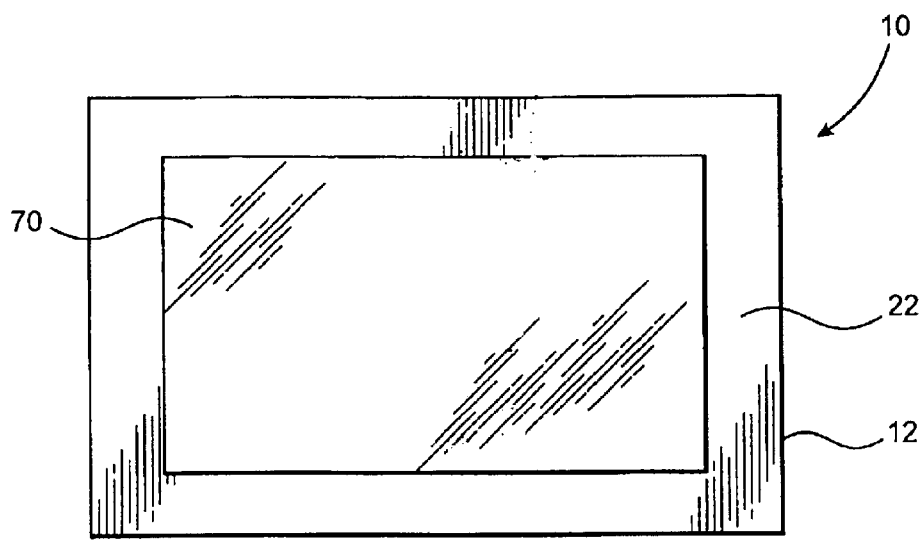
FIG. 4 is a rear plan view of at least the embodiment of FIG. 1 showing the exterior surface portions thereof.

Still referring to the embodiment of FIGS. 1 through 4, the access assembly further includes an additional access structure in the form of a cover or lid 44 which may be selectively positionable between an open position, as shown in FIG. 3, and a closed position, as shown in FIG. 1. The cover member 44 may extend along a length of at least a portion of the periphery of the container 12 or be otherwise located to overly and cover both the handle portion 32 and the one or more cleaning heads 34 and 35. The cover member 44 may have a disposition, dimension and configuration such that the entire cleaning implement 30 is enclosed whether or not the handle portion 32 and the one or more cleaning heads 34 and 35 are located in a same compartment 18,20 or segregated compartments 18 and 20. In addition, the cover member 44 may be hingedly or pivotally attached to the container 12 as at 46 and/or may be removable therefrom to provide clear access to the cleaning implement 30.

With primary reference to the embodiments of FIGS. 5 through 7, the dental care kit assembly 10' includes a container 12' having a plurality of segregated compartments or areas 50, 52 and 54 for the containment of the various operative components. As shown in FIG. 5, the various operative components may include at least one dental floss supply 26, the cleaning implement 30', which comprises a handle portion 32' and at least one but preferably a plurality of cleaning heads 34, 35, 35', etc. The cleaning heads may of course vary in number but preferably the structural features thereof comprise a plurality of bristles or other cleaning portions or members, as set forth above. As such, the cleaning heads 34, 35, 35', are equivalent to the cleaning heads described with regard to the embodiment of FIGS. 1 through 4. Further, each of the cleaning heads 34, 35, 35' includes a stem portion 38 designed to be removably but firmly secured within a socket 36 preferably, but not necessarily formed in one end of the handle portion 32'. In addition, the container 12' includes a base or under portion 22 and a front panel portion 24 structurally equivalent to that described as part of the embodiment of FIGS. 1 through 4.

Further with regard to the embodiment of FIGS. 5 through 7, the access assembly comprises a plurality of access structures including at least one access structure defined by the access opening or aperture 40 and stop member 40' as set forth above. The access assembly also includes a cover member 44' which is disposed to at least cover or enclose compartment 54. Also, the compartment 52 may be disposed such that the handle portion 32' and both compartments 52, 54 would be covered and/or at least partially enclosed by the cover member 44'. As with the embodiment of FIGS. 1 through 4, the cover member 44' is pivotally, hingedly or otherwise movably or removably connected as at 46 to the container 12'. In addition, the access assembly may include a separate, removable access structure 43 when the handle portion 32' and/or compartment 52 are not disposed beneath the cover member 44'.

The access assembly of the present invention further comprises yet an additional access structure in the form of a seal assembly generally indicated as 60 in FIG. 7. The seal assembly and includes at least one but preferably a plurality of hermetic seals 62, 64, 66, which are adhered in a substantially air tight sealing engagement in overlying relation to each of one or more chambers. The chambers 65 are therefore segregated and may in fact be specifically designed to contain the cleaning heads 34, 35, 35' in a somewhat sterile environment due to the hermetic seal members 62, 64, and 66. Removal of the seal members 62, 64, 66, etc. is accomplished by dislodging a peripheral portion or tab 68 thereof and applying at least a minimal pulling force thereto. Sufficient force applied to the tab 68 will remove respective ones of the seal members 62, 64, 66 from their initial, sealed positions relative to the respective chambers 65. It should be further noted that a single seal member such as at 62 may extend over and provide a substantially air tight seal for all of the one or more cleaning heads 34, 34' 35' etc. rather providing a plurality of individual seal member 62, 64 and 66.

Common to both of the above noted preferred embodiments are further structural features including a reflective surface 70 on some exposed or exposable portion of the container 12 and/or 12'. The reflective surface 70 should be sufficiently reflective to allow the observation of a visual image, such as of a user's mouth. In doing so, any of a wide variety of different cleaning procedures, utilizing the kit assembly 10 and/or 10' of the present invention, may be practiced with more precision.

By way of example only, in at least one embodiment of the present invention the handle portion 32' as shown in FIG. 5 may have a somewhat pointed end configuration 37 thereby enabling its use as a toothpick type of instrument. When utilizing the handle portion 32' as a toothpick, the user may be aided by viewing his or her own teeth, gums, etc. in the reflective surface 70. Also, in the embodiments of FIGS. 1 through 4, the reflective surface 70 is located on or considered a part of the base 22. However, it should be noted that the reflective surface 70 can be located at a variety of other locations on either of the containers 12 or 12'. An example would be locating a similar reflective surface 70' on a portion of the cover member 44', such as on the undersurface thereof, as indicated in FIG. 6.

Other structural features associated with both of the dental care kit assemblies 10 and 10' preferably include the outer or frontal panel 26 being formed of an at least partially transparent and/or translucent type material. This would allow the viewing or observation of anyone or all of the operative components stored within the containers 12 or 12' in order to accurately determine their location and/or the quantity or number of such components still available for use.

In addition, in at least one preferred embodiment of the present invention, especially where the outer panel or cover 24 overlying the supply of dental floss 26 is not made of transparent material, other provisions are included to indicate the depletion of the dental floss supply 26. More specifically, the trailing end of the supply of dental floss 26 may include an indicator, such as by including a color coding so as to indicate that a trailing end segment of the dental floss strand 27 and/or the dental floss supply 26 is being approached. By way of example only, almost the entire length, or at least the majority of the length of the strand 27 may be formed of a first color (or a natural color), wherein a last or end portion of predetermined length may include an indicator comprising a different color, which is clearly visually distinguishable from the leading remainder of the dental floss strand 27.

A modification of the indicator would include a predetermined length of the strand 27 defining a trailing end segment being formed of or including a different, clearly distinguishable flavor or "taste". As such, any portion of the strand 27 preceding the trailing end segment would have no flavor or a different flavor from that of the trailing end segment. In the latter modification of at least one preferred embodiment, those users who are visually handicapped could therefore clearly determine when the end of the dental floss supply 26 or dental floss strand 27 is approaching and/or being utilized.

Yet another structural feature associated with both of the embodiments of FIGS. 1 and 5 includes a reinforcement assembly or structure 76 integrally or otherwise fixedly formed on or connected to an appropriate location of the containers 12 and 12'. The reinforcement structure 76 may be formed from an at least partially rigid piece of plastic or other appropriate material and be disposed and structured to resist bending, folding or collapse of the containers 12 and 12' in order to reduce the possibility of damage to the operative components contained therein as well as maintain the structural integrity of the individual containers 12 or 12'.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A dental care kit assembly comprising:
   a) a container having a predetermined size and configuration,
   b) at least one supply of dental floss disposed within said container and including a rotatable spool having a dental floss strand removably mounted thereon,
   c) a cleaning implement disposed within said container in segregated relation to said spool,
   d) said container comprising an access assembly including independent access structures for said dental floss strand and said cleaning implement,
   e) said independent access structures comprising at least a first access disposed to facilitate a removal of a strand segment from said rotatable spool, and
   f) a stop member disposed substantially adjacent said first access in retaining engagement with a strand segment of said dental floss strand disposed exteriorly of said container.

2. A kit assembly as recited in claim 1 wherein said container is formed of a material having sufficient rigidity to resist folding.

3. A kit assembly as recited in claim 2 wherein said container, supply of dental floss and said cleaning implement are disposable.

4. A kit assembly as recited in claim 2 wherein said predetermined reduced size configuration comprises said container having a reduced thickness limited primarily by the dimension and configuration of its contents.

5. A kit assembly as recited in claim 4 wherein said container further comprises a reinforcement assembly connected thereto and disposed and structured to resist collapsing or folding of said container.

6. A kit assembly as recited in claim 5 wherein said container, said rotatable spool and said cleaning implement are independently disposable.

7. A kit assembly as recited in claim 1 wherein said stop member includes a severing portion disposed in engagable relation with said strand segment.

8. A kit assembly as recited in claim 1 wherein said independent access structures comprise a second access disposed and structured to selectively provide and restrict access to said cleaning implement.

9. A kit assembly as recited in claim 1 further comprising a reflective surface mounted on said container and structured to facilitate observance of a visual image therein.

10. A dental care kit assembly comprising:
    a) a container having a predetermined size and configuration,
    b) at least one supply of dental floss disposed within said container and including a rotatable spool having a dental floss strand removably mounted thereon,
    c) a cleaning implement disposed within said container in segregated relation to said spool, said cleaning implement comprising a handle portion and at least one cleaning head removably securable to said handle portion, and
    d) said container comprising an access assembly including independent access structures for said dental floss strand and said cleaning implement.

11. A kit assembly as recited in claim 10 wherein said handle portion and said one cleaning head are disposed in segregated relation to one another within said container.

12. A kit assembly as recited in claim 11 wherein said independent access structures include a hermetic seal disposed to isolate said one cleaning head from an exterior of said container.

13. A kit assembly as recited in claim 12 wherein said hermetic seal is disposed to isolate said one cleaning head from other contents of said container.

14. A kit assembly as recited in claim 10 wherein said cleaning implement comprises a plurality of cleaning heads each removably securable to said handle portion for independent application thereof.

15. A kit assembly as recited in claim 14 wherein at least one of said cleaning heads comprises a reduced size collection of bristles.

16. A kit assembly as recited in claim 14 wherein said access structure comprises a seal assembly including a plurality of hermetic seals sufficient in number to independently isolate each of said plurality of cleaning heads from one another and from an exterior of said container.

17. A kit assembly as recited in claim 10 wherein said handle is configured and dimensioned to define a tooth pick.

18. A dental care kit assembly comprising:
    a) a container having a predetermined size and configuration and including a plurality of compartments,
    b) at least one supply of dental floss disposed within one of said plurality of compartments and including a rotatable spool removably supporting a dental floss strand,
    c) a cleaning implement including a handle portion and at least one cleaning head removably attachable to said handle portion,
    d) said handle portion and said one cleaning head disposed within said plurality of compartments in at least partially segregated relation to one another, and
    e) an access assembly mounted on said container and disposed and structured to provide independent removal of said dental floss strand and said cleaning implement from said container and facilitate segregation thereof from one another.

19. A kit assembly as recited in claim 18 wherein said access assembly comprises separated access structures comprising a first access disposed to facilitate removal of a strand segment from said spool.

20. A kit assembly as recited in claim 19 further comprising a stop member disposed substantially adjacent said first access structure in retaining engagement with a strand segment of said dental floss strand exiting said container, said stop member including a severing portion disposed in engagable relation with said strand segment.

21. A kit assembly as recited in claim 19 further comprising a second access including a cover member movably mounted on said container and selectively positionable between an open positioned and a closed position.

22. A kit assembly as recited in claim 21 wherein said separated access structures further comprise a third access including a hermetic seal disposed to substantially isolate at least some contents of said container from an exterior thereof.

23. A kit assembly as recited in claim 18 wherein said access assembly comprises a hermetic seal disposed to isolate said one cleaning head from an exterior of said container.

24. A kit assembly as recited in claim 18 wherein said cleaning implement comprises a plurality of cleaning heads each removably securable to said handle portion for independent application thereof.

25. A kit assembly as recited in claim 24 wherein said access assembly comprises a seal assembly including a plurality of hermetic seals sufficient in number to independently isolate each of said cleaning heads from one another and from an exterior of said container.

26. A kit assembly as recited in claim 18 wherein said predetermined reduced size configuration is at least partially defined by said container having a substantially flat, reduced thickness limited primarily by the dimension and configuration of its contents.

27. A kit assembly as recited in claim 18 wherein said container further comprises a reinforcement assembly connected thereto and disposed and structured to resist collapse or folding of said container.

28. A kit assembly as recited in claim 18 wherein said container is formed of an at least semi-rigid material resistant to folding; said container, said supply of dental floss and said cleaning implement each formed of a disposable material.

29. A disposable dental care kit assembly comprising:
a) a container having a substantially flat configuration comprising a plurality of compartments,
b) at least one dental floss supply including a rotatable spool having a dental floss strand removably mounted thereon,
c) a cleaning implement including a handle portion and a plurality of cleaning head each removably attachable to said handle portion,
d) said one dental floss supply, said handle portion and said plurality of cleaning heads disposed within separate ones of said plurality of compartments and in at least partially segregating relation to one another,
e) said access assembly comprising a plurality of access structures each disposed in communicating relation with at least one of said cleaning implement and said one dental floss supply, and
f) said plurality of access structures further disposed to provide independent access to corresponding ones of said plurality of compartments.

30. A kit assembly as recited in claim 29 comprising a plurality of dental floss supplies disposed in different ones of said plurality of compartments, each of said plurality of dental floss supplies being accessible through a different one of said plurality of access structures.

31. A kit assembly as recited in claim 30 wherein at least two of said plurality of dental floss supplies each include a rotatable spool having a dental floss strand removably mounted thereon.

32. A kit assembly as recited in claim 29 wherein said access assembly comprises a seal assembly including a plurality of hermetic seals cooperatively disposed and structured with corresponding ones of said plurality of compartments and being sufficient in number to independently isolate each of said cleaning heads from one another and from an exterior of said container.

33. A kit assembly as recited in claim 29 wherein said handle is configured and dimensioned to at least partially define a tooth pick.

34. A kit assembly as recited in claim 29 wherein said container further comprises a reinforcement assembly connected thereto and disposed and structured to resist collapsing or folding of said container.

35. A kit assembly as recited in claim 29 wherein said dental floss strand includes an indicator formed thereon, said indicator disposed and structured to facilitate recognition of at least a trailing end segment of said dental floss strand.

36. A kit assembly as recited in claim 35 wherein said indicator is structured to visually distinguish said trailing end segment from a remainder of said dental floss strand.

37. A kit assembly as recited in claim 35 wherein said indicator is structured to distinguish said trailing end segment from a remainder of said dental floss strand by flavor.

38. A dental care kit assembly comprising:
a) a container having a predetermined size and configuration,
b) at least one supply of dental floss disposed within said container and including a rotatable spool having a dental floss strand removably mounted thereon,
c) a cleaning implement disposed within said container in segregated relation to said spool,
d) said container comprising an access assembly including independent access structures for said dental floss strand and said cleaning implement,
e) said independent access structures comprising a first access and a second access, said first access disposed to facilitate a removal of a strand segment from said rotatable spool,
f) said second access disposed and structured to selectively provide and restrict access to said cleaning implement, and
g) said second access comprising a cover member pivotally mounted on said container and selectively positionable between an open position and a closed position.
h) said independent access structures further comprise a third access including a hermetic seal disposed to substantially isolate at least some contents of said container from an exterior thereof.

39. A dental care kit assembly comprising:
a) a container having a predetermined size and configuration,
b) at least one supply of dental floss disposed within said container and including a rotatable spool having a dental floss strand removably mounted thereon,
c) a cleaning implement disposed within said container in segregated relation to said spool, d) said container comprising an access assembly including independent access structures for said dental floss strand and said cleaning implement,
e) said independent access of structures comprising a first access, a second access and a third access, and
f) said first access disposed to facilitate a removal of a strand segment from said rotatable spool and said third access including a hermetic seal disposed to substantially isolate at least some content of said container from an exterior thereof.

h) said independent access structures further comprise a third access including a hermetic seal disposed to substantially isolate at least some contents of said container from an exterior thereof.

40. A kit assembly as recited in claim 39 wherein said hermetic seal is disposed to isolate at least a portion of said cleaning implement.

* * * * *